United States Patent [19]

Rehder et al.

[11] 4,274,164
[45] Jun. 23, 1981

[54] ENDOPROSTHESIS FOR A HIP JOINT, ESPECIALLY FOR THE HIP JOINT OF A HUMAN BEING

[75] Inventors: Günther Rehder, Stuhr; Johann Rusdea, Wiesbaden, both of Fed. Rep. of Germany

[73] Assignee: Orthoplant Orthopädische Implantate GmbH & Co. KG, Bremen, Fed. Rep. of Germany

[21] Appl. No.: 42,811

[22] Filed: May 29, 1979

[30] Foreign Application Priority Data

Aug. 4, 1978 [DE] Fed. Rep. of Germany ....... 2834298

[51] Int. Cl.$^3$ .............................................. A61F 1/03
[52] U.S. Cl. ................................ 3/1.913; 128/92 CA
[58] Field of Search ..................... 128/92 C, 92 CA; 3/1.913, 1.912

[56] References Cited

U.S. PATENT DOCUMENTS

| Re. 28895 | 7/1976 | Noiles | 128/92 CA X |
|---|---|---|---|
| 2,668,531 | 2/1954 | Haboush | 3/1.912 |
| 3,053,251 | 9/1962 | Black et al. | 128/92 CA |
| 3,521,302 | 7/1970 | Muller | 128/92 C X |
| 3,871,031 | 3/1975 | Boutin | 128/92 CA X |
| 3,918,102 | 11/1975 | Eichler | 3/1.912 |
| 4,123,806 | 11/1978 | Amstutz et al. | 3/1.912 |
| 4,141,088 | 2/1979 | Treace et al. | 128/92 CA X |
| 4,170,794 | 10/1979 | Zeibig et al. | 128/92 CA X |

FOREIGN PATENT DOCUMENTS

| 876739 | 5/1953 | Fed. Rep. of Germany. | |
|---|---|---|---|
| 923383 | 2/1955 | Fed. Rep. of Germany. | |
| 1566386 | 5/1970 | Fed. Rep. of Germany. | |
| 2259313 | 6/1973 | Fed. Rep. of Germany. | |
| 7313647 | 9/1973 | Fed. Rep. of Germany. | |
| 2512407 | 9/1976 | Fed. Rep. of Germany. | |
| 2527865 | 12/1976 | Fed. Rep. of Germany. | |
| 2411617 | 4/1977 | Fed. Rep. of Germany. | |
| 1107877 | 4/1955 | France | 128/92 C |
| 2297030 | 8/1976 | France | 3/1.912 |
| 2361861 | 3/1978 | France | 3/1.912 |

OTHER PUBLICATIONS

Publication MOT, Mecron Hip Prosthesis, p. XXVI, Feb. 1975.
Publication "Der Chirurg", No. 7, Jul., 1975.

Primary Examiner—Clifford D. Crowder
Attorney, Agent, or Firm—Toren, McGeady and Stanger

[57] ABSTRACT

An endoprosthesis for a hip joint is disclosed. The endoprosthesis includes a first cap-shaped, femur head shell which is arranged on the free end of the femur head and partially overlaps the femur head. The first femur head shell has a convex outer side. A shell-shaped pan forms part of the prosthesis which has a concave inner side for supporting the first femur head shell. The pan is arranged on the free end of the acetabulum. A second cap-shaped femur head shell is included which extends outwardly beyond the edge of the first femur head shell. The second femur head shell is arranged between the first femur head shell and the femur head. The various features of the shells and pan are disclosed.

8 Claims, 5 Drawing Figures

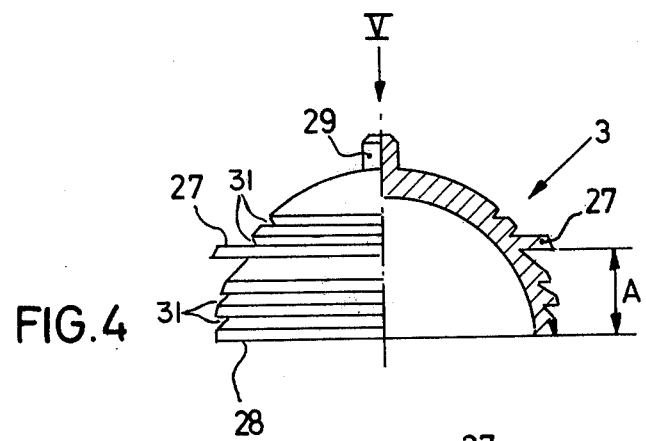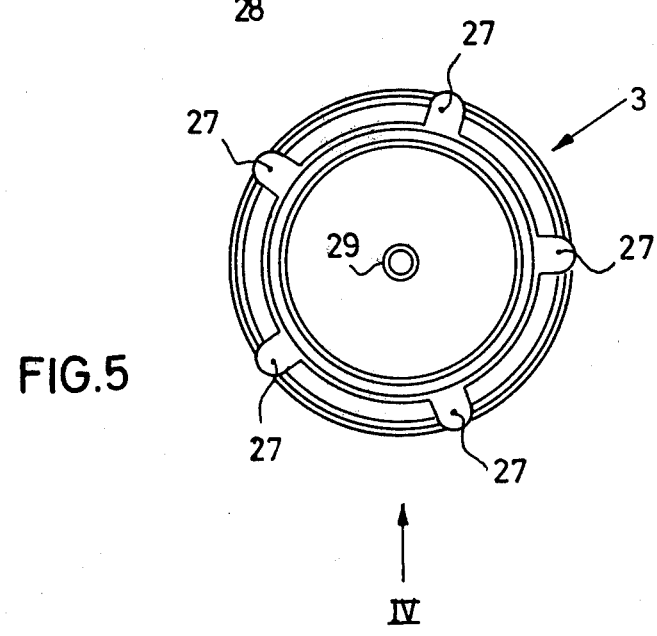

ENDOPROSTHESIS FOR A HIP JOINT, ESPECIALLY FOR THE HIP JOINT OF A HUMAN BEING

FIELD OF THE INVENTION

The invention relates to an endoprosthesis for a hip joint, especially for the hip joint of a human being, including a cap-shaped shell which is arranged on the free end of the femur head and partially overlaps the femur head. The cap-shaped shell has an outer side, which acts as a (first) sliding area and is supported in a concave inner side of a shell-shaped pan which is arranged on the free end of the acetabulum. The concave inner side acts as a (second) sliding area.

Furthermore, the invention relates to a shell-shaped pan, especially suitable for such prosthesis.

BACKGROUND OF THE INVENTION

So-called total endoprostheses are known for different diseases and injuries of a hip joint. These total endoprostheses consist of two portions, namely, of a shell which (usually after previous cutting) is to be cemented in the hip pan and usually consists of plastic material which is compatible with tissue, and of an elongate, relatively large, prosthesis portion which consists of a suitable steel alloy. On one end of this prosthesis portion, there is arranged a sphere or ball which replaces the femur head of the injured bone. The sphere is connected through a passage part and a flange to a curved shaft which, after previous separation of the head of the femur neck, is inserted in the bone and is anchored there with bone cement.

Compared to the previously known possibilities for treatment of such fractures and diseases, like arthrosis and the like, very good results have been achieved by means of these known total endoprostheses. It cannot be denied, however, that the rate of complications is great enough so that improvements are necessary.

Consideration must be given to the fact that the operation of inserting such a total endoprosthesis in the respective body is, in almost all respects, very serious. This is so because bone parts of the hip joint of a considerable extent have to be removed which, for example, in the case of wear phenomena, are not injured per se and would be suitable for the intended supporting function.

Apart from fractures of the femur neck which obviously represent special circumstances and which frequently require such an operation (especially in so-called long fractures), there still remains great fields of use for diseases which basically do not require such a radical operation.

Therefore, such radical operations are no longer considered in such hip joint diseases, and it has been tried to replace only the sliding areas, which are especially important for the operability of the hip joint and are simultaneously highly stressed. This can be accomplished by cementing a shell-shaped pan of suitable plastic material or of ceramics into the hip joint pan, similar to the previously described total endoprosthesis. Also included in the procedure is the replacing of the counter-sliding area for the artificial hip joint pan by a shell which consists of metal, namely, of suitable steel, which has on its outer side the shape of a spherical segment. The height of the spherical segment usually is a little smaller than the equatorial height, i.e, smaller than the radius of curvature of the outer side of the spherical segment.

In the interior, the known metal shell for the femur head has a cylindrical bore which, on the end face, leads into a spherical surface section.

The curvature of this spherical area section on the inner side of the known femur head shell corresponds to a curvature on the femur head after a respective cutting of the end face of the femur head. The diameter of the cylindrical internal wall of the known femur head shell corresponds to the diameter of the femur head, after respective cutting.

Such a hip joint prosthesis, also known as a shell prosthesis, has obviously the advantage, in comparison with the above-described total endoprosthesis, that considerably less bone tissue has to be removed and, therefore, considerably less foreign material has to be inserted into the body.

It turns out in practice, however, that these theoretical advantages are again compensated to a considerable extent by disadvantages of these known shell prostheses.

First of all, no precise fitting surfaces can be produced during the cutting of the cylindrical and spherical end sections of the bone, because the freely guided cutting instrumentation does not have such qualities and because this instrumentation removes tissue material just where the smallest working resistance occurs. This more or less free working, however, not only leads to imprecise fitting areas but it is impossible to construct the implant physiologically in axis alignment.

Furthermore, the inner edge of the metal shell which is applied fittingly on the previously treated bone exerts, in the case of subsequent static and dynamical loads, a groove or notch effect on the bone which leads to groove fracture some time afterwards.

Moreover, a disadvantage in this known hip joint prosthesis is that the metal shell, also like the hip pan shell, is anchored with cement and, in fact, usually with a significant amount of cement which leads again to an insufficient amount of the tissue of the femur neck head. In the region of the bone shaft, this often leads to a spongiosis of the bone with subsequent disintegration which, in turn, results in incorrect positioning of the supporting surfaces or errors in the bone removal processes. However, both phenomena are, of course, extremely disadvantageous because the bradytrophic tissue of the cartilage has to absorb and transfer, in addition to its function of movement, the occurring forces and moments.

OBJECTS OF THE INVENTION

Therefore, the primary object of the present invention is to create a hip joint endoprosthesis of the type described of a so-called shell prosthesis, wherein the previously mentioned and other unmentioned disadvantages are avoided, without losing the basic advantages of a shell prosthesis in comparison to a total endoprosthesis. According to this object, the prosthesis according to the invention does not use, or hardly uses, fixing material like bone cement which is not compatible with tissue. Furthermore, the danger of a grooving or notching effect should be completely avoided. Moreover, the hip joint prosthesis according to the invention, shall include a certain damping action which does not occur in the known prosthesis of the previously described type. Finally, with the endoprosthesis according to the invention, there is the possibility that the total implant is constructed in physiological axis alignment under simultaneous creation of precise fitting surfaces so that misalignments are practically eliminated.

These and other advantages shall be ensured, according to the objects, not only with regard to the femur head shell, but also with regard to the synthetic hip pan wherein the hip pan, according to the invention, cannot only be used in the total hip joint endoprosthesis, but also in other constructions, namely, for example, in a construction of the above described known type.

SUMMARY OF THE PRESENT INVENTION

These objects can be solved according to the invention thereby that between the femur head shell, provided in the acetabulum pan and the femur head, there is arranged a second cap-shaped femur head shell which does not consist of metal, and extends outwardly over the edge of the first femur head shell. This second femur head shell consists, preferably, of a plastic material compatible with tissue, for example, polyethylene. This ensures that no grooving actions can take place on the neck of femur and, moreover, that the desired damping action is achieved. The latter is especially accomplished when the thickness of the second femur head shell diminishes outwardly in radial direction from the center.

Thus, in accordance with the invention, an endoprosthesis for a hip joint, especially for the hip joint of a human body, comprises a first cap-shaped femur head shell which is arranged on the free end of the femur head and partially overlaps the femur head. The first femur head shell has a convex outer side which acts as a first sliding area. A shell-shaped pan is also included, having a concave inner side for supporting the first femur head shell. The pan is arranged on the free end of the acetabulum. The concave inner side of the pan acts as a second sliding area. Finally included is a second cap-shaped, femur head shell which extends outwardly beyond the edge of the first femur head shell. The second femur head shell is arranged between the first femur head shell, which is supported in the acetabulum pan and the femur head.

For a better understanding of the present invention, reference is made to the following description and accompanying drawings, while the scope of the present invention will be pointed out in the appended claims.

BRIEF DESCRIPTION OF THE DRAWINGS

In the drawings:

FIG. 4 shows a lateral view of the pan, partially in section, in the direction of the arrow IV in FIG. 5; and FIG. 5 shows a top view of the pan according to FIG. 4, in the direction of the arrow V in FIG. 4.

DESCRIPTION OF THE PREFERRED EMBODIMENTS

Figure 1:
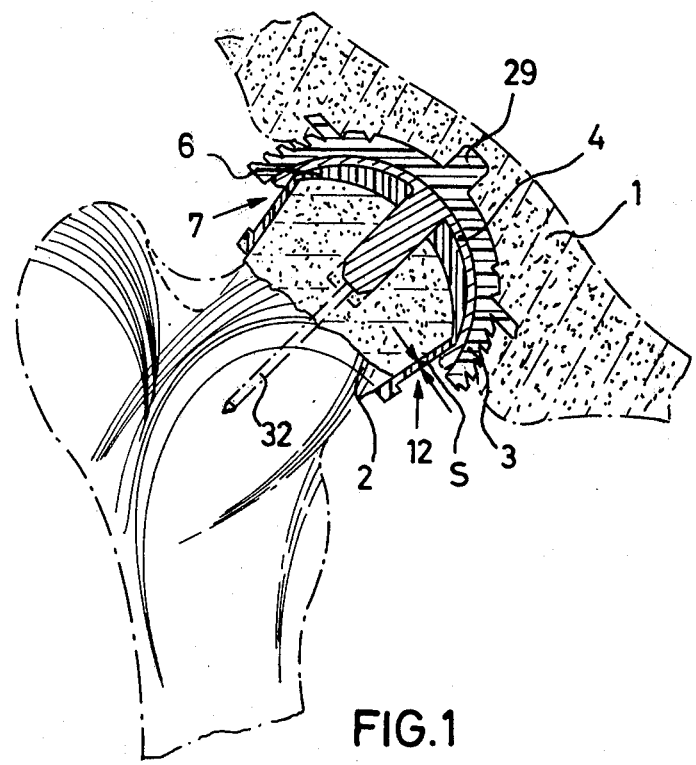
FIG. 1 shows a diagrammatic section of a hip joint endoprosthesis according to the invention in the inserted state.

Referring initially to FIG. 1, shown there in dotted lines is a hip joint, in diagrammatic view, provided with an endoprosthesis according to the invention. Specifically shown, partially in section, are the acetabulum 1 and the femur head 2.

Figure 2:
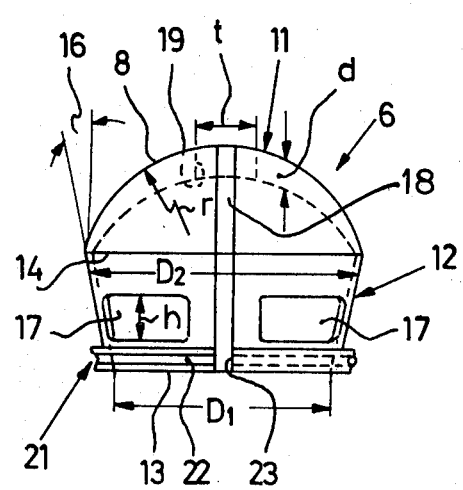
FIG. 2 shows a side view of the second femur head shell.

The hip joint prosthesis consists essentially of a shell-shaped pan 3 (also shown in FIGS. 4 and 5) which is inserted into the acetabulum 1, a first femur head shell 4 (also shown in FIG. 3), and a second femur head shell 6 (also shown in FIG. 2).

As can be seen from FIG. 1 of the drawing, the cap-shaped second femur head shell 6 is arranged between the first femur head shell 4 and the tissue of the femur head 2, which tissue is treated in a manner which will be described below. The femur head shell 6 extends outwardly or downwardly, respectively, beyond the edge 7 of the first femur head shell. The first femur head shell consists, preferably, of metal and, in particular, of the material CrCoMo 28. The second femur head shell 6 as well as the acetabulum pan 3 consists, preferably, of polyethylene and, in particular, of the type RCH 1000, so that the contact surfaces of adjacent structural parts, especially the cooperating sliding areas of the acetabulum pan 3 and the first femur head shell 4, consists of suitably different materials so as to guarantee advantageous sliding properties. The material CrCoMo28 refers to a chromium-cobalt alloy, which is in common use as Endocast while the designation RCH 1000 signifies an Ultra High Molecular Weight Polyethylene (UHMWPE), accented in total joint arthroplasty.

As is obvious from FIGS. 1 and 2, the thickness d of the second femur head shell 6 diminishes outwardly in radial direction from the center.

The outer side 8 of the second femur head shell 6 is essentially in alignment and form-congruent to the end face of the femur head 2, upon which spherical indentations have been made. This outer side 8 has a curvature r of about 27 mm and corresponds with the curvature r of the inner side 9 of the first femur head shell 4. Subsequent to the outwardly tapering section 11 of the second femur head shell 6, which section overlaps the end face of the femur head 2, there is a jacket which, as a surface, fits in assembled condition, on the treated side surface of the femur head 2 and is essentially cylindrical. The actual shape of the jacket deviates, however, from, a precise cylindrical form according to the invention, because the jacket 12 of the second femur head shell 6, at least on its inner side and, in the present case, however, also on its outer side, is constructed conically. This results in the jacket having on its edge 13, a smaller diameter $D_1$ than on its upper end, i.e., on the transition area 14 to the end section 11 where, accordingly, the diameter $D_2$ is larger. The conicalness or the angle 16, respectively, of the jacket 12 relative to the perpendicular line, i.e., to the axis of symmetry of the second femur head shell 6, is preferably 12° in the present embodiment.

The thickness d of the second femur head shell 6 is relatively small in the region of its jacket 12 and is approximately only 1 mm, while the thickness of the second femur head shell 6 increases from the transition area 14 inwardly to approximately 5 mm.

The jacket 12 of the second femur head shell 6 has four window-like through-openings 17 which are essentially uniformly spaced apart over the periphery and which have a height h of 8 mm and a length of about 18 mm. Further, the second femur head shell 6 has a radial slot 18 of 3 mm in width and a central through-opening 19 which, preferably, has a diameter t of 11 mm.

The second femur head shell has on the edge 21 a contrast wire, wherein FIG. 2 of the drawing shows two possibilities. In the left part of FIG. 2, the edge section 21 is provided with a channel 22 in which there is inserted a contrast wire which can be fixed in form-locking manner. The right part of FIG. 2 shows a development in which a contrast wire 23 is already incorporated in the edge section 21 so that it is not necessary for the operating surgeon to apply the contrast wire.

Figure 3:
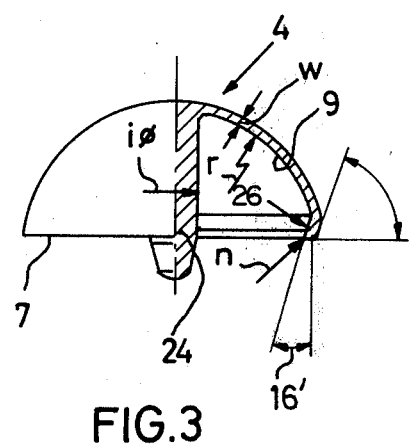
FIG. 3 illustrates a side view of the first femur head shell, partially in section.

The first femur head shell 4, shown especially in FIG. 3, is provided on its inner side 9 with a centrally arranged centering or guide pin 24 which is integrally constructed with the cap-shaped section of the first femur head shell 4 and which has, according to this embodiment, a diameter i of 8.3 mm. The centering pin 24 is conically constructed on its end section and protrudes outwardly over the edge 7 as can be seen from FIG. 3.

Moreover, the first femur head shell 4 has the shape of a hollow spherical indentation having a basic wall thickness w of 1 mm wherein, however, the edge section is reinforced. The spherically-shaped section of the first femur head shell 4 leads over, on its inner side, to a conical edge section at a distance to the edge 7, according to FIG. 3. The conicalness is equal to the conicalness of the jacket 12 of the second femur head shell so that the angle 16', in the present embodiment, is also 12° relative to the horizontal line or to the axis of symmetry, respectively.

The conical edge section 26 of the inner side of the first femur head shell 4, then passes over with an outwardly bevelled convex edge section into the face end or into the actual edge 7, respectively, of the first femur head shell wherein the radius n is 10 mm.

Once more, it is mentioned that the first femur head shell 4 need not necessarily be composed of steel or of a similar metal but, instead, can be composed, for example, of ceramics.

The acetabulum pan 3 is provided on its outer side with five lug-shaped or nose-shaped projections 27 with a distance A of approximately 14 mm to the edge 28 and with a thickness of 2.3 mm, as shown in FIG. 4. All projections 27 have the same distance A to the edge 28 and are spaced relative to each other with the same distance along the periphery of the acetabulum pan 3. As is obvious from FIG. 4, the projections are bevelled on their end section, in order to snap simply into the groove of the acetabulum, which groove will be described below. These projections act as resilient spring tongues which, when the acetabulum pan 3 is pressed into the acetabulum 1, jump into the groove to be provided in the acetabulum.

In the top view (FIG. 5), the projections 27 are rounded so that they can easily conform to the shape of the annular groove which is created in the acetabulum during the operating procedure.

Furthermore, on the outer side of the acetabulum pan 3, there is arranged a centering pin 29 having a diameter and length of 6 mm. Moreover, the outer side of the acetabulum pan 3 is provided on both sides of the projections 27 with recesses 31 which are constructed as concentric grooves. Recesses 31, adjacent to the edge 28, are constructed in such a manner that the remaining sections can act also as "barbs" if, over time, spongiosis has built up and has grown into the recesses.

The acetabulum pan 3 is essentially developed in the shape of a hollow hemisphere, as can be seen especially from FIG. 4, wherein the basic wall thickness is about 4 mm.

The hip joint endoprosthesis according to the invention, is inserted with suitable instrumentation as follows:

At the start of the actual operation, a Kirschner wire 32 is shot into the neck of the femur, which is shown in FIG. 1 with dash-dotted lines. This Kirschner wire 32 is not located in the joint after the prosthesis is in the final position.

The Kirschner wire 32 serves only for guiding a shank-cutter with which a central guiding hole is cut in the head of the neck of the femur, which hole later serves for guiding the guide pin 24 of the first femur head shell 4.

Then the head of the neck of the femur is rounded with a crown saw or a suitable cutter, respectively, to provide a curvature radius which corresponds with the curvature of the inner side of the end section 11 of the second femur head shell 6.

With a suitable instrumentation which is guided on the Kirschner wire 32, both cutting processes can be performed simultaneously which not only shorten the operating time but also reduce the load on the guiding bore for the guide pin 24 to a minimum.

Moreover, on the side surface of the head of the femur neck there must be created a fitting area for the second femur head shell 6. This can also be achieved simultaneously by a suitable instrumentation or it can be created by a cylindrical jacket of the head of the femur neck having the diameter $D_2$, at least simultaneously by the same instrumentation and, therefore, in the same operating cycle. Then this jacket can be worked conically in a second operating cycle through a boring head whose cutter can be adjusted with regard to its conicalness so that the boring head can be removed again from the bone after production of the conical fitting area of the head of the femur neck, without damaging the neck of the femur.

Moreover, the natural pan of the acetabulum 1 must be prepared, i.e., first it must be worked with a suitable spherical head milling cutter whose curvature is equal to the curvature of the outer side of the synthetic acetabulum pan 3.

After cutting, the edge of the bearing point is then suitably rounded for the synthetic acetabulum pan 3, which can be done also with a suitable cutting implement.

Afterwards, a central guiding hole for the guide pin or centering pin 29 of the acetabulum pan 3 is drilled. This bore has not only the task to center the acetabulum pan 3 during insertion but also to serve as a guide for a guide pn of a suitable groove milling cutter which is inserted with reeled-in cutters in the previous worked recess of the acetabulum. The thickness of the cutters corresponds to the thickness of the projections 27. During rotation of the groove milling cutter, their cutting elements slowly drive out. It is assured, by suitable adjusting, that they do not exceed a defined maximum radial extension whereby the desired depth of the grooves is secured. If this is achieved, the cutting elements are again retracted into the groove milling cutter which can then be removed out of the acetabulum 1 again.

After the Kirschner wire 32 has also been removed, the second femur head shell 6 can be put on the head of the femur neck and afterwards the first femur head shell 4 can be put thereon in a form-locking manner. Suitably, this can be achieved by a weak impact with a suitable inserting implement wherein the fitting is extremely simple because of the fact that the femur head shell is rounded on the inner side of its lower edge. Nevertheless, there is achieved a very tight seat because of the conical fitting areas.

The insertion of the acetabulum pin 3 is obtained in a similar manner, for example, with a suitable set-head wherein the centering is guaranteed by the centering pin 29 and wherein the spring tongues of the projections 27 are bent and snap into the previously created groove in a form-locking manner.

It is obvious that with the hip joint endoprosthesis according to the invention, there is no need for cementing. Under certain circumstances, it might be advisable to use some additional cementing. In any case, only a small amount of bone cement is necessary which does not affect the tissue structure in a disadvantageous way.

It can be seen that with the hip joint endoprosthesis according to the invention, a physiologically, axis-aligned structure of the implant can be easily achieved wherein a neck of the femur which is reprofiled has also, in a biomechanical respect, better properties in comparison to the shell prosthesis of the known type. Because of the increased radius of the spherical indentation, oblique forces are prevented. This results in an advantageous biomechanical anatomy which need not deviate or deviates only a little from the normal anatomy. The less such oblique forces occur and the less cement that is used, the less is the probability that there occur any complications after insertion of such a prosthesis.

As already mentioned above, bone cement should not be used at all, or at least hardly be used, in the endoprosthesis according to the invention. Therefore, the present invention provides a form-locking connection between the second femur head shell and the femur head as well as between the acetabulum pan and the acetabulum.

With regard to the second femur head shell, this can be accomplished according to the invention in that, subsequent to the section of the second femur head shell which overlaps the end face of the femur head, there is arranged a jacket which fits on the treated femur head in the assembled condition. The jacket, at least its inner side of the second femur head shell, extends conically convergent to the free edge, i.e., the jacket of the second femur head shell has at its edge a smaller diameter than at the transition from the jacket to the remaining section of the second femur head shell.

It turns out that, on the one hand, for a tight fit and, on the other hand, to remove only little tissue, for the above-mentioned reasons, it is completely sufficient to have a conical angle of the jacket of the second femur head shell of between 8° and 20°, wherein a conical angle of about 12° is preferred.

The jacket of the second femur head shell is preferably provided with several window-type through openings. It turns out that spongiosis grows into this window. Accordingly, the anchoring is even improved while any rotational movement of the second femur head shell on the femur head is avoided.

Because of the conicalness of the jacket of the second femur head shell and the resulting conditions, namely, that the free diameter at the edge of the second femur head shell is smaller than the largest diameter of the treated femur head, the second femur head shell is preferably provided with a radial slot, for example, about 3 mm wide, so that it can expand during assembly and can slip over the largest diameter of the treated femur head.

In order to guarantee the desired construction of the implant which should be physiologically in axial alignment, the second femur head preferably has a central through-opening for a centering pin of the first femur head shell, wherein the above-mentioned radial slot suitably extends to this through-opening.

As mentioned above, the first femur head shell has, preferably on its inner side, a centrally arranged, protruding guide pin which serves for guiding and centering, respectively, according to the drawing and is not used for fixing and anchoring the first femur head shell. It should be mentioned that such embodiment can also be provided according to the invention if, for any reason, two femur head shells are not provided but only one, since also in such a prosthesis, the same advantageous properties can be achieved as obtained with a preferred double shell prosthesis (more exactly expressed, triple shell prosthesis) which has already been mentioned.

This guide pin extends downwardly from the inner side of the (first) femur head shell which preferably is composed of metal or ceramics and preferably protrudes a little over the edge of the (first) femur head shell, wherein the free end section of the guide pin is preferably conically or pointedly constructed. The (first) femur head shell has in a preferred further development of the present invention, an edge section which runs on its inner side conically toward the inside. The conicalness is equal to the conicalness of the jacket of the second femur head shell (or equal to the conicalness of the treated bone when a second femur head shell is not used).

In order to simplify placing or pressing of the first femur head shell on the second femur head shell, after the second shell has already been slipped over the treated femur head, the inner surface of the conically extending edge section of the first femur head shell is preferably provided with an annular recess of partially circular cross-section. The recess extends into the end face of the first femur head shell wherein the radius of curvature of this annular recess can be, for example, about 10 mm.

As already mentioned above, the shell-shaped pan is not cemented, according to the invention, into the hip joint pan, but is kept therein in form-locking manner. Therefore, the present invention provides several projections on the outer side of the pan which are preferably arranged at a distance from the pan edge, and not only have the same distance to the edge of the pan but also have approximately the same distance to each other, so that the projections are uniformly spaced over the periphery of the pan.

These projections preferably have an essentially uniform thickness and are tongue-shaped or lug-shaped. The projections protrude a few mm over the actual, essentially spherical, outer side of the pan or over the periphery on which the projections are arranged. Because of this design, the projections are relatively resilient and can be characterized as spring tongues which can engage, as has been described, a groove which is provided in the tissue.

Preferably, there is also centrally arranged on the outer side of the pan, a centering spigot or centering pin which is integrally constructed with the pan.

Moreover, the outer side of the pan is provided with recesses, according to a preferred development, namely, with concentric grooves or the like which have not only good flexibility and, therefore, good adjustment to the opposed "spherical head", but simultaneously also guarantee an exceptional abrasion behavior. Furthermore, spongiosis grows into these recesses some time afterwards, so that an additional anchoring of the pan in the tissue is guaranteed.

While the foregoing description and drawings represent the preferred embodiments of the present invention, it will be obvious to those skilled in the art that various changes and modifications may be made therein without departing from the true spirit and scope of the present invention.

LIST OF REFERENCE NUMERALS

1—Acetabulum
2—Femur head
3—Acetabulum pan
4—First femur head shell
6—Second femur head shell
7—Edge (of 4)
8—Outer side (of 6)
9—Inner side (of 4)
11—End section (of 6)
12—Jacket
13—Edge
14—Transition area
16, 16'—Angle
17—Through-openings
18—Radial slot
19—Through-opening
21—Edge
22—Channel
23—Contrast wire
24—Guide pin
26—Conical edge section
27—Projections
28—Edge
29—Centering pin
31—Recesses
32—Kirschner wire

What is claimed is:

1. A femur head cap for a hip joint endoprosthesis which can be implanted without cement, comprising:
an inner plastic shell to be placed on a femur head, said inner shell including a top section the inner surface of which conforms to the end face of the femur head and the outer surface of which is generally hemispherically shaped, and a jacket extending from said top section for fitting about a treated circumferential surface of the femur head, the inner surface of said jacket conically narrowing in the direction away from said top section, said inner shell having a slot which extends between the free edge of said jacket and the center of said top section to enable said jacket to expand to slip over the largest diameter of the femur head when said inner shell is placed over the femur head; and
a metallic outer shell having a generally hemispherical inner surface which corresponds to the outer surface of said top section of said inner shell so that said outer shell can be fitted over said top section, said outer shell also having a generally hemispherical outer surface wherein the height of said outer shell as measured from the free end plane to the center of the outer surface of said outer shell is less than the radius of curvature of the outer surface of said outer shell, said outer shell including an end section adjacent the free end thereof for engaging the outer surface of said jacket of said inner shell, the inner surface of said end section conically narrowing in the direction toward the free end of said outer shell, and a pin extending from the center of the inner surface of said outer shell for engaging said inner shell when said outer shell is fitted over said inner shell to operatively align both of said shells.

2. A femur head cap according to claim 1, wherein the inner surface of said jacket of said inner shell is conically tapered at an angle of between about 8° to 20° relative to the axis of said jacket.

3. A femur head cap according to claim 2, wherein the inner surface of said jacket is conically tapered by about 12°.

4. A femur head cap according to claim 1, wherein said slot in said inner shell has a width of between about 2 to 4 mm.

5. A femur head cap according to claim 1, wherein said outer shell is arranged to be rotatable relative to said inner shell about the axis of said pin.

6. A femur head cap according to claim 1, wherein said pin extends through said top section of said inner shell over a distance less than the distance between the center of the inner surface of said inner shell and the plane which includes the free edge of said jacket of said inner shell.

7. A femur head cap according to claim 1, wherein said pin of said outer shell has a diameter of between about 5 to 10 mm.

8. A femur head cap according to claim 1, wherein said jacket of said inner shell includes a number of through openings which are substantially uniformly spaced apart from one another over the periphery of said jacket for allowing spongiosis to grow within said through openings to increase anchoring of said jacket on the femur head.

* * * * *